US010004711B2

(12) United States Patent
Weiser et al.

(10) Patent No.: US 10,004,711 B2
(45) Date of Patent: Jun. 26, 2018

(54) METHODS AND COMPOSITIONS COMPRISING 10-HYDROXY-2-DECENOIC ACID

(71) Applicant: DSM IP ASSETS B.V., Heerlen (NL)

(72) Inventors: Michael Weiser, Lafaette, CO (US); Christopher Butt, Erie, CO (US)

(73) Assignee: DSM IP Assets B.V., Heerlen (NL)

( * ) Notice: Subject to any disclaimer, the term of this patent is extended or adjusted under 35 U.S.C. 154(b) by 0 days. days.

(21) Appl. No.: 15/309,470

(22) PCT Filed: May 7, 2015

(86) PCT No.: PCT/US2015/029790
§ 371 (c)(1),
(2) Date: Nov. 8, 2016

(87) PCT Pub. No.: WO2015/171960
PCT Pub. Date: Nov. 12, 2015

(65) Prior Publication Data
US 2017/0181995 A1    Jun. 29, 2017

Related U.S. Application Data

(60) Provisional application No. 61/990,283, filed on May 8, 2014.

(51) Int. Cl.
*A61K 31/201* (2006.01)
*A61K 31/202* (2006.01)

(52) U.S. Cl.
CPC .......... *A61K 31/201* (2013.01); *A61K 31/202* (2013.01)

(58) Field of Classification Search
None
See application file for complete search history.

(56) References Cited

U.S. PATENT DOCUMENTS

| | | | |
|---|---|---|---|
| 2005/0065212 A1 | 3/2005 | Pineau et al. | |
| 2014/0271844 A1 | 9/2014 | Miller | |

FOREIGN PATENT DOCUMENTS

| | | | |
|---|---|---|---|
| CN | 1836671 A | 9/2006 | |
| CN | 101570482 A | 11/2009 | |
| CN | 102408395 A | 4/2012 | |
| DE | 19844022 C1 | 5/2000 | |
| FR | 2773484 | * 7/1999 | ........... A61K 31/095 |
| FR | 2829491 | 3/2003 | |
| GB | 1033843 | 6/1966 | |
| GB | 1145623 | 3/1969 | |
| JP | 10114652 A2 | 5/1998 | |
| JP | 2005287411 A2 | 10/2005 | |
| JP | 2006219471 A2 | 8/2006 | |
| JP | 2008228694 A2 | 10/2008 | |
| JP | 2009274961 | 11/2009 | |
| JP | 2010111646 | 5/2010 | |
| JP | 2012110253MT | 11/2010 | |
| JP | 2012207004 A2 | 10/2012 | |
| WO | WO9848788 | 11/1998 | |
| WO | WO2004021803 A1 | 3/2004 | |
| WO | WO2007045693 A1 | 4/2007 | |
| WO | WO2007130581 | 11/2007 | |
| WO | WO2009014105 A1 | 1/2009 | |
| WO | WO2013003689 A2 | 1/2013 | |
| WO | WO2013138157 | 9/2013 | |

OTHER PUBLICATIONS

Barbier, Vingt-Cinq Ans Apres: Histoire De La Decouverte de La substance Royale, Apidologie, 1986, 1-12, 17(1).
Barker, Identification of 10-Hydroxy-Δ2-decenoic Acid in Royal Jelly, Nature, 1959, 996-997, 183.
Boch et al., Pheromonal control of queen rearing in honeybee colonies, Journal of Agricultural Research, 1976, 59-62, 15(2).
Duplan et al., Effects of Hydroxydecine(R) (10-hydroxy-2-decenoic acid) on skin barrier structure and function in vitro and clinical efficacy in the treatment of UV induced xerosis, Eur. J. Dermatol., 2011, 906-15, 6.
Elnagar, Samar, Royal jelly counteracts bucks' "summer infertility", Animal Reproduction Science, 2010, 174-180, 121.
Fang et al., Chinese Pharmacological Bulletin, 1994, 139-42, 10(2).
Furukawa, Stimulatory Effects of Royal Jelly on the Generation of Neuronal and Glial Cells—Expectation of Protection Against Some Neurological Disorders, Food & Food Ingredients Journal of Japan, 2008, 620-626, 213(7), Dai Nippon Printing Co.
Guo et al., Royal Jelly Supplementation Improves Lipoprotein Metabolism in Humans, J. Nutr Sci Vitaminol, 2007, 345-348, 53.
Hashimoto et al., Oral Administration of Royal jelly Facilitates mRNA Expression of Glial Cell Line-Derived Neurotrophic Factor and Neurofilament H in the Hippocampus of the Adult Mouse Brain, Biosci. Biotechnol. Biochem., 2005, 800-805, 69(4).
Hattori et al., Royal Jelly Facilitates Restoration of the Cognitive Ability in Trimethyltin-Intoxicated Mice, eCAM, 2009, 1-5.
Honda et al., Lifespan-Extending Effects of Royal Jelly and Its Related Substances on the Nematode Caenorhabditis elegans, PLoS ONE, 2011, 1-10, 6(8).
Husein et al., A new approach to enhance reproductive performance in sheep using royal jelly in comparison with equine chorionic gonadotropin, Animal Reproduction Science 93, 2006, 24-33, 93.
Inoue et al., Royal Jelly prolongs the life span of C3H/HeJ mice: Correlation with reduced DNA damage, Experiemtnal Gerontology, 2003, 965-969, 38.
Isidorov et al., Gas chromatographic-mass spectrometric investigation of volatile and extractable compounds of crude royal jelly, Journal of Chromatography B, 2012, 109-116, 885-886.
Ito et al., Antidepressant-Like Activity of 10-Hydroxy-Trans-2-Decenoic Acid, a Unique Unsaturated Fatty Acid of Royal Jelly, in Stress-Inducible Depression-Like Mouse Model, Evidence-Based Complementary and Alternative Medicine, 2012, 1-6, 2012.

(Continued)

*Primary Examiner* — Brian J Davis
(74) *Attorney, Agent, or Firm* — Shannon McGarrah

(57) ABSTRACT

Disclosed herein are compositions for use in treating anxiety, inflammatory conditions, fertility-related disorders, for increasing cognitive performance and managing weight comprising 10-Hydroxy-2-decenoic acid or a derivative thereof and preferably at least one polyunsaturated fatty acid. The preferred polyunsaturated fatty acid is DHA.

25 Claims, No Drawings

(56) References Cited

OTHER PUBLICATIONS

Izuta et al., 10-Hydroxy-2-decenoic Acid, a Major Fatty Acid from Royal Jelly Inhibits VEGF-induced Angiogenesis in Human Umbilical Vein Endothelial Cells, eCAM, 2009, 489-494, 6(4).
Kai et al., Royal jelly enhances antigen-specific mucosal IgA response, Food Science & Nutrition, 2013, 222-227, 1(3).
Karaca et al., Effect of royal jelly on experimental colitis induced by acetic acid and alteration of mast cell distribution in the colon of rats, European Journal of Histochemistry, 2010, 54:e35.
Mishima et al., Roayl jelly has estrogenic effects in vitro and in vivo, Journal of Ethnopharmacology, 2005, 215-220, 101.
Morita et al., Effect of royal jelly ingestion for six months on healthy volunteers, Nutrition Journal, 2012, 77, 11.
Munstedt et al., Royal Jelly Reduces the Serum Glucose Levels in Healthy Subjects, Journal of Medicinal Food, 2009, 1170-1172, 12(5).
Nagai et al., Antioxidant Properties of Enzymatic Hydrolysates from Royal Jelly, Journal of medicinal Food, 2006, 363-367, 9(3).
Nakaya et al., Effect of Royal Jelly on Bisphenol A-Induced Proliferation of Human Breast Cancer Cells, Biosci. Biotechnol. Biochem., 2007, 253-255, 71(1).
Naumann et al., Effects of Synthetic, Honey Bee (Hymenoptera: Apidae) Queen Mandibular-Gland Pheromone on Workers in Packages, Journal of Economic Entomology, 1990, 1271-75, 83(4).
Niu et al., Royal Jelly Prevents the Progression of Sarcopenia in Aged Mice in Vivo and In Vitro, Journals of Gerontology: Biological Sciences, 2013, 1-11.
Spannhoff et al., Histone deacetylase inhibitor activity in royal jelly might facilitate caste switching in bees, EMBO Reports—Scientific Reports, 2011, 238-243, 12(3).
Sugiyama et al., Inhibitory effect of 10-hydroxy-trans-2-decenoic acid on LPS-induced IL-6 production via reducing IkB expression, Innate Immunity, 2012, 429-437, 18(3).
Sugiyama et al., Inhibitory Mechanism of 10-Hydroxy-trans-2-decenois-Acid (Royal Jelly Acid) Against Lipopolysaccharide- and Interferon-B-Induced Nitric Oxide Production, Inflammation, 2013, 372-378, 36(2).
Suzuki et al., Estogenic Activities of Fatty Acids and a Sterol Isolated from Royal Jelly, eCAM, 2007, 295-302, 5(3).
Takahashi et al., Inhibition of interferon-γ-induced nitric oxide production by 10-hydroxy-trans-2-decenoic acid through inhibition of interferon regulatory factor-8 induction, Cellular Immunology, 2012, 73-78, 273.
Takahashi et al., Inhibitory effect of 10-hydroxydecanoic acid on lipopolysaccharide-induced nitric oxide production via translational downregulation of interferon regulatory factor-1 in RAW264 murine macrophages, Biomedical Research, 2013, 205-214, 34(4).
Taniguchi et al., Oral administration of royal jelly inhibits the development of atopic dermatitis-like skin lesions in NC/Nga mice, International Immunopharmacology 3, 2003, 1313-1324, 3.
Townsend et al., Activity of 10-Hydroxydecenois Acid from Royal Jelly against Experiemental Leukemia and Ascitic Tumours, Nature, 1959, 1270-1, 183(4670).
Townsend et al., studies on the inVitro Antitumor Activity of Fatty Acids I., Cancer Research, 1960, 503-510, 20.
Trhlin et al., Chemical communication in the honeybee, Verterinarni Medicina, 2011, 265-273, 6.
Veylon, Biochemcial regulation of social behavior by pherormones, Nouvelle Presse Medicale, 1972, 2993-5, 1(4).
Wang et al., Connective tissue growth factor, a regulator related with 10-hydroxy-2-decenois acid down-regulate MMPs in rheumatoid arthritis, Rheumatol Int., 2012, 2791-2799, 32(9).
Yang et al., 10-Hydroxy-2-decenoic acid from Royal Jelly: A potential medicine for RA, Journal of Ethnopharmacology, 2010, 314-321, 128.
Yang et al., Hetero-specific queen retinue behavior of worker bees in mixed-species colonies of Apis cerana and Apis mellifera, Apidologie, 2010, 54-61, 41.
Zhang et al., Guangzhou Chemical Industry, 2013, 20-22, 41(9).

* cited by examiner

METHODS AND COMPOSITIONS COMPRISING 10-HYDROXY-2-DECENOIC ACID

This application is a National Stage of International Application No. PCT/US2015/029790, which claims the benefit of 35 U.S.C. § 119(e) to U.S. Provisional Patent Application No. 61/990,283 filed May 8, 2014, the entire contents of each of which are hereby incorporated by reference.

This application claims the benefit of the filing date of U.S. Provisional Patent Application No. 61/990,283 filed May 8, 2014, the disclosure of which is hereby incorporated herein by reference.

Disclosed herein are compositions for treating anxiety, inflammatory conditions and fertility-related disorders, and for increasing cognitive performance and managing weight comprising 10-Hydroxy-2-decenoic acid and at least one polyunsaturated fatty acid. Further disclosed herein are methods for treating anxiety, inflammatory conditions and fertility-related disorders, and for increasing cognitive performance and managing weight, comprising administration of 10-Hydroxy-2-decenoic acid, wherein such method may further comprise administration of at least one polyunsaturated fatty acid.

Queen bee acid (10-hydroxy-2-decenoic acid) is the predominant fatty acid constituent of royal jelly. Royal jelly is harvested from a select population of cells that specifically support the growth and development of queen bee larvae and is provided to the queen bee by the drones. Royal jelly is believed to play a role in the enhanced size, fertility and lifespan of queen bees. It is believed that queen bee acid (10-hydroxy-2-decenoic acid) is one of the principal active components of royal jelly.

Queen bee acid inhibits histone deacetylases and is now recognized as the epigenetic switch for the queen bee larvae phenotype (Spannhoff et al., Histone Deacetylase Inhibitor Activity in Royal Jelly Might Facilitate Caste Switching in Bees, *EMBO Reports*, Vol. 12, No. 3, 2011). Other in vitro effects of queen bee acid include antitumor activity (Townsend et al., Studies on the in vitro Antitumor Activity of Fatty Acids: I. 10-Hydroxy-2-decenoic Acid from Royal Jelly, *Cancer Res*, 1960; 20:503-510; Izuta et al., 10-Hydroxy-2-decenoic Acid, a Major Fatty Acid from Royal Jelly Inhibits VEGF-induced Angiogenesis in Human Umbilical Vein Endothelial Cells, *eCam*, 2009; 6(4)489-494) and stimulation of neurogenesis from stem cells while inhibiting gliogenesis (Hattori et al., Royal Jelly Facilitates Restoration of the Cognitive Ability in Trimethyltin-Intoxicated Mice, *eCAM* 2009). These findings suggest that queen bee acid may be an active component of royal jelly.

It has now been found that queen bee acid (10-hydroxy-decenoic acid) has an effect in the treatment of anxiety, inflammatory conditions and fertility-related disorders, and may increase cognitive performance and help manage weight, wherein managing weight is maintaining weight in a subject having a diseased state, or weight loss, particularly where such weight loss is due to age or stress.

The queen bee acid can be in the form of a free fatty acid, salt, fatty acid ester (e.g., methyl or ethyl ester), monoacylglycerol (MAG), diacyglycerol (DAG) triacylglycerol (TAG), and/or phospholipid (PL) or mixtures thereof. Preferably, the queen bee acid is in the free fatty acid or salt form.

Disclosed herein are compositions for treating anxiety, inflammatory conditions and fertility-related disorders, and for increasing cognitive performance and managing weight comprising 10-Hydroxy-2-decenoic acid and at least one polyunsaturated fatty acid. Further disclosed herein are methods for treating anxiety, inflammatory conditions and fertility-related disorders, and for increasing cognitive performance and managing weight, comprising administration of 10-Hydroxy-2-decenoic acid, wherein such method may further comprise administration of at least one polyunsaturated fatty acid.

In a preferred embodiment, the composition comprises 10-Hydroxy-2-decenoic acid or a derivative thereof, and at least one polyunsaturated fatty acid (PUFA). Preferably, the composition comprises a PUFA that is an omega-3 fatty acid. More preferably, the composition comprises an omega-3 fatty acid with 20 or 22 carbon atoms. Most preferably, the composition comprises a PUFA that is an omega-3 fatty acid and is all-cis-docosa-4,7,10,13,16,19-hexaenoic acid, also known as docosahexaenoic acid (DHA).

In one embodiment, the methods disclosed herein comprise administration of 10-Hydroxy-2-decenoic acid or a derivative thereof for treating anxiety, inflammatory conditions and fertility-related disorders, and for increasing cognitive performance and managing weight.

In one embodiment, the methods further comprise administration of at least one polyunsaturated fatty acid (PUFA). Preferably, the PUFA is an omega-3 fatty acid. More preferably, the PUFA is all-cis-docosa-4,7,10,13,16,19-hexaenoic acid, also known as docosahexaenoic acid (DHA).

Disclosed herein are compositions for treating anxiety, inflammatory conditions and fertility-related disorders, and for increasing cognitive performance and managing weight comprising 10-Hydroxy-2-decenoic acid or a derivative thereof, and at least one polyunsaturated fatty acid (PUFA). Further disclosed herein are methods for treating anxiety, inflammatory conditions and fertility-related disorders, and for increasing cognitive performance and managing weight, wherein such methods comprise administration of 10-Hydroxy-2-decenoic acid or a derivative thereof, and further comprising administration of at least one polyunsaturated fatty acid.

In a further embodiment, compositions are provided comprising about 0.2 mg to about 5000 mg 10-Hydroxy-2-decenoic acid and about 100 mg to about 4000 mg DHA in the form preferably of one or more capsules. Preferably, the respective amounts are about 12 mg to about 300 mg 10-Hydroxy-2-decenoic acid mg and about 100 mg to about 1500 mg DHA. In the one or more capsules, the 10-Hydroxy-2-decenoic acid may be provided in a form of a free acid or an ester. In particular, the free acid preferably is provided separate from DHA. In case both components are provided as esters, the QBA-ester may be combined with DHA in one dosage form. An advantage of providing the components in ester-form is that the components show improved stability, and can be provided in combined capsules.

The features and advantages of the invention may be more readily understood by those of ordinary skill in the art upon reading the following detailed description. It is to be appreciated that certain features of the invention that are, for clarity reasons, described above and below in the context of separate embodiments, may also be combined as to subcombinations thereof.

Embodiments identified herein as exemplary are intended to be illustrative and not limiting.

The term "about" is intended to capture variations above and below the stated number that may achieve substantially the same results as the stated number.

The term "therapeutically-effective amount" refers to that amount of a compound sufficient to modulate one or more of the symptoms of the condition or disease being treated. A "therapeutically-effect amount" and/or dosage range for compounds used in the method of treatment of the invention may be determined by one of ordinary skill in the art via known criteria including age, weight, and response of the individual patient, and interpreted within the context of the disease being treated and/or prevented.

"10-Hydroxy-2-decenoic acid" may be alternatively referred to as "Queen Bee Acid" or "QBA". It is understood that 10-Hydroxy-2-decenoic acid is the chemical formula for "Queen Been Acid ("QBA")".

Fatty acids are classified based on the length and saturation characteristics of the carbon chain. Fatty acids present in a microbial oil can have from 4 to 28 carbon atoms and are termed short chain, medium chain, or long chain fatty acids based on the number of carbons present in the chain. Fatty acids are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

Polyunsaturated fatty acids (PUFAs) are classified based on the position of the first double bond from the methyl end of the fatty acid; omega-3 (n-3) fatty acids contain a first double bond at the third carbon, while omega-6 (n-6) fatty acids contain a first double bond at the sixth carbon. For example, docosahexaenoic acid (DHA) is an omega-3 long chain polyunsaturated fatty acid (LC-PUFA) with a chain length of 22 carbons and 6 double bonds, often designated as "22:6n-3."

In one embodiment, the PUFA is selected from an omega-3 fatty acid, an omega-6 fatty acid, and mixtures thereof. In another embodiment, the PUFA is selected from long-chain polyunsaturated fatty acids (LC-PUFAs). In another embodiment, the LC PUFA has 20 carbon atoms or more, preferably C20 or C22 carbon atoms. In a still further embodiment, the PUFA is selected from docosahexaenoic acid (DHA), eicosapentaenoic acid (EPA), docosapentaenoic acid (DPA), arachidonic acid (ARA), gamma-linolenic acid (GLA), dihomo-gamma-linolenic acid (DGLA), stearidonic acid (SDA), and mixtures thereof. In another embodiment, the PUFA is selected from DHA, ARA, and mixtures thereof. In a further embodiment, the PUFA is ARA. In yet a further embodiment, the PUFA is DHA.

The PUFAs can be in the form of a free fatty acid, salt, fatty acid ester (e.g., methyl or ethyl ester), monoacylglycerol (MAG), diacylglycerol (DAG), triacylglycerol (TAG), and/or phospholipid (PL), or mixtures thereof. Preferably, the PUFA is in the ethyl ester or glyceryl ester form, like the TAG form.

Any source of PUFA can be used in the compositions and methods of the invention, including, for example, animal, plant and microbial sources. Preferred polyunsaturated fatty acid (PUFA) sources can be any source of PUFA that are suitable for use in the present invention.

Examples of animal sources include aquatic animals (e.g., fish, marine mammals, crustaceans, rotifers, etc.). Examples of plant sources include microalgae, flaxseeds, rapeseeds, corn, evening primrose and borage. Examples of microorganisms include microalgae, protists, bacteria and fungi (including yeast). The use of a microorganism source, such as microalgae, can provide organoleptic advantages. Preferably, the polyunsaturated fatty acid source comprises microalgae or microalgal oils.

Preferably, when microorganisms are the source of polyunsaturated fatty acids, the microorganisms are cultured in a fermentation medium in a fermenter. Alternatively, the microorganisms can be cultured photosynthetically in a photobioreactor or pond. Preferably, the microorganisms are lipid-rich microorganisms, more preferably, the microorganism are selected from the group consisting of microalgae, bacteria, fungi and protists, more preferably, the microorganisms are selected from the group consisting of dioflagellates, yeast and fungi of the genus *Mortierella*. Preferably, the microorganisms comprise microorganisms of the genus *Crypthecodinium* and order Thraustochytriales and filamentous fungi of the genus *Mortierella*, and more preferably, microorganisms are selected from the genus *Thraustochytrium, Schizocythrium*, or mixtures thereof.

In accordance with the present invention, the polyunsaturated fatty acids that are used in the compositions described herein are in a variety of forms, for example, such forms include, but are not limited to, a highly purified algal oil comprising a PUFA, a plant oil comprising the PUFA, triglyceride oil comprising the PUFA, phospholipid comprising the PUFA, a combination of protein and phospholipids comprising the PUFA, dried marine microalgae comprising the PUFA, sphingolipids comprising the PUFA, esters of the PUFA, free fatty acid, a conjugate of the PUFA with another bioactive molecule, and conjugates thereof.

Disclosed herein are compositions for treating anxiety, inflammatory conditions and fertility-related disorders, and for increasing cognitive performance and managing weight comprising 10-Hydroxy-2-decenoic acid or a derivative thereof, and at least one polyunsaturated fatty acid (PUFA).

One embodiment is directed to a composition comprising 10-Hydroxy-2-decenoic acid or a derivative thereof, and at least one polyunsaturated fatty acid (PUFA) for treating anxiety. Preferably, the PUFA is an omega-3 fatty acid. More preferably, the PUFA is all-cis-docosa-4,7,10,13,16,19-hexaenoic acid, also known as docosahexaenoic acid (DHA).

Another embodiment is directed to a composition comprising 10-Hydroxy-2-decenoic acid or a derivative thereof, and at least one polyunsaturated fatty acid (PUFA) for treating anxiety wherein the 10-Hydroxy-2-decenoic acid or derivative thereof is administered in an amount of about 0.2 mg/day to about 5000 mg/day and the PUFA is administered in an amount of about 100 mg/day to about 4000 mg/day.

Another embodiment is directed to a composition comprising 10-Hydroxy-2-decenoic acid or a derivative thereof, and docosahexaenoic acid for treating anxiety wherein the 10-Hydroxy-2-decenoic acid or derivative thereof is administered in an amount of about 0.2 mg/day to about 5000 mg/day and the docosahexaenoic acid is administered in an amount of about 100 mg/day to about 4000 mg/day.

Another embodiment is directed to a composition comprising 10-Hydroxy-2-decenoic acid or a derivative thereof, and at least one polyunsaturated fatty acid (PUFA) for treating anxiety wherein the 10-Hydroxy-2-decenoic acid or derivative thereof is administered in an amount of about 12 mg/day to about 300 mg/day and the PUFA is administered in an amount of about 100 mg/day to about 1500 mg/day.

Another embodiment is directed to a composition comprising 10-Hydroxy-2-decenoic acid or a derivative thereof, and docosahexaenoic acid for treating anxiety wherein the 10-Hydroxy-2-decenoic acid or derivative thereof is administered in an amount of about 12 mg/day to about 300 mg/day and the docosahexaenoic acid is administered in an amount of about 100 mg/day to about 1500 mg/day.

Another embodiment is directed to a composition comprising 10-Hydroxy-2-decenoic acid or a derivative thereof, and at least one polyunsaturated fatty acid (PUFA) for treating an inflammatory condition. Preferably, the PUFA is an omega-3 fatty acid. More preferably, the PUFA is all-cis-docosa-4,7,10,13,16,19-hexaenoic acid, also known as docosahexaenoic acid (DHA).

Another embodiment is directed to a composition comprising 10-Hydroxy-2-decenoic acid or a derivative thereof, and at least one polyunsaturated fatty acid (PUFA) for treating an inflammatory condition wherein the 10-Hydroxy-2-decenoic acid or derivative thereof is administered in an amount of about 0.2 mg/day to about 5000 mg/day and the PUFA is administered in an amount of about 100 mg/day to about 4000 mg/day.

Another embodiment is directed to a composition comprising 10-Hydroxy-2-decenoic acid or a derivative thereof, and docosahexaenoic acid for treating an inflammatory condition wherein the 10-Hydroxy-2-decenoic acid or derivative thereof is administered in an amount of about 0.2 mg/day to about 5000 mg/day and the docosahexaenoic acid is administered in an amount of about 100 mg/day to about 4000 mg/day.

Another embodiment is directed to a composition comprising 10-Hydroxy-2-decenoic acid or a derivative thereof, and at least one polyunsaturated fatty acid (PUFA) for treating an inflammatory condition wherein the 10-Hydroxy-2-decenoic acid or derivative thereof is administered in an amount of about 12 mg/day to about 300 mg/day and the PUFA is administered in an amount of about 100 mg/day to about 1500 mg/day.

Another embodiment is directed to a composition comprising 10-Hydroxy-2-decenoic acid or a derivative thereof, and docosahexaenoic acid for treating an inflammatory condition wherein the 10-Hydroxy-2-decenoic acid or derivative thereof is administered in an amount of about 12 mg/day to about 300 mg/day and the docosahexaenoic acid is administered in an amount of about 100 mg/day to about 1500 mg/day.

Preferably, the inflammatory condition comprises a gastrointestinal disorder. More preferably, the inflammatory condition is colitis.

Another embodiment is directed to a composition comprising 10-Hydroxy-2-decenoic acid or a derivative thereof, and at least one polyunsaturated fatty acid (PUFA) for increasing cognitive performance Preferably, the PUFA is an omega-3 fatty acid. More preferably, the PUFA is all-cis-docosa-4,7,10,13,16,19-hexaenoic acid, also known as docosahexaenoic acid (DHA).

Another embodiment is directed to a composition comprising 10-Hydroxy-2-decenoic acid or a derivative thereof, and at least one polyunsaturated fatty acid (PUFA) for increasing cognitive performance wherein the 10-Hydroxy-2-decenoic acid or derivative thereof is administered in an amount of about 0.2 mg/day to about 5000 mg/day and the PUFA is administered in an amount of about 100 mg/day to about 4000 mg/day.

Another embodiment is directed to a composition comprising 10-Hydroxy-2-decenoic acid or a derivative thereof, and docosahexaenoic acid for increasing cognitive performance wherein the 10-Hydroxy-2-decenoic acid or derivative thereof is administered in an amount of about 0.2 mg/day to about 5000 mg/day and the docosahexaenoic acid is administered in an amount of about 100 mg/day to about 4000 mg/day.

Another embodiment is directed to a composition comprising 10-Hydroxy-2-decenoic acid or a derivative thereof, and at least one polyunsaturated fatty acid (PUFA) for increasing cognitive performance wherein the 10-Hydroxy-2-decenoic acid or derivative thereof is administered in an amount of about 12 mg/day to about 300 mg/day and the PUFA is administered in an amount of about 100 mg/day to about 1500 mg/day.

Another embodiment is directed to a composition comprising 10-Hydroxy-2-decenoic acid or a derivative thereof, and docosahexaenoic acid for increasing cognitive performance wherein the 10-Hydroxy-2-decenoic acid or derivative thereof is administered in an amount of about 12 mg/day to about 300 mg/day and the docosahexaenoic acid is administered in an amount of about 100 mg/day to about 1500 mg/day.

Preferably, the increasing cognitive performance comprises increased speed of learning, improved memory retention, and combinations thereof.

Another embodiment is directed to a composition comprising 10-Hydroxy-2-decenoic acid or a derivative thereof, and at least one polyunsaturated fatty acid (PUFA) for managing weight. In one embodiment, managing weight is managing weight in a subject having a diseased state. In another embodiment, managing weight is weight loss. In one embodiment, the weight loss is associated with aging. In another embodiment, the weight loss is associated with stress. Preferably, the PUFA is an omega-3 fatty acid. More preferably, the PUFA is all-cis-docosa-4,7,10,13,16,19-hexaenoic acid, also known as docosahexaenoic acid (DHA).

Another embodiment is directed to a composition comprising 10-Hydroxy-2-decenoic acid or a derivative thereof, and at least one polyunsaturated fatty acid (PUFA) for managing weight wherein the 10-Hydroxy-2-decenoic acid or derivative thereof is administered in an amount of about 0.2 mg/day to about 5000 mg/day and the PUFA is administered in an amount of about 100 mg/day to about 4000 mg/day. In one embodiment, managing weight is managing weight in a subject having a diseased state. In another embodiment, managing weight is weight loss. In one embodiment, the weight loss is associated with aging. In another embodiment, the weight loss is associated with stress.

Another embodiment is directed to a composition comprising 10-Hydroxy-2-decenoic acid or a derivative thereof, and docosahexaenoic acid for managing weight wherein the 10-Hydroxy-2-decenoic acid or derivative thereof is administered in an amount of about 0.2 mg/day to about 5000 mg/day and the docosahexaenoic acid is administered in an amount of about 100 mg/day to about 4000 mg/day. In one embodiment, managing weight is managing weight in a subject having a diseased state. In another embodiment, managing weight is weight loss. In one embodiment, the weight loss is associated with aging. In another embodiment, the weight loss is associated with stress.

Another embodiment is directed to a composition comprising 10-Hydroxy-2-decenoic acid or a derivative thereof, and at least one polyunsaturated fatty acid (PUFA) for managing weight wherein the 10-Hydroxy-2-decenoic acid or derivative thereof is administered in an amount of about 12 mg/day to about 300 mg/day and the PUFA is administered in an amount of about 100 mg/day to about 1500 mg/day. In one embodiment, managing weight is managing weight in a subject having a diseased state. In another embodiment, managing weight is weight loss. In one embodiment, the weight loss is associated with aging. In another embodiment, the weight loss is associated with stress.

Another embodiment is directed to a composition comprising 10-Hydroxy-2-decenoic acid or a derivative thereof, and docosahexaenoic acid for managing weight wherein the 10-Hydroxy-2-decenoic acid or derivative thereof is administered in an amount of about 12 mg/day to about 300 mg/day and the docosahexaenoic acid is administered in an amount of about 100 mg/day to about 1500 mg/day. In one embodiment, managing weight is managing weight in a subject having a diseased state. In another embodiment, managing weight is weight loss. In one embodiment, the weight loss is associated with aging. In another embodiment, the weight loss is associated with stress.

Another embodiment is directed to a composition comprising 10-Hydroxy-2-decenoic acid or a derivative thereof, and at least one polyunsaturated fatty acid (PUFA) for treating fertility-related disorders. Preferably, the PUFA is an omega-3 fatty acid. More preferably, the PUFA is all-cis-docosa-4,7,10,13,16,19-hexaenoic acid, also known as docosahexaenoic acid (DHA).

Another embodiment is directed to a composition comprising 10-Hydroxy-2-decenoic acid or a derivative thereof, and at least one polyunsaturated fatty acid (PUFA) for treating fertility-related disorders wherein the 10-Hydroxy-2-decenoic acid or derivative thereof is administered in an amount of about 0.2 mg/day to about 5000 mg/day and the PUFA is administered in an amount of about 100 mg/day to about 4000 mg/day.

Another embodiment is directed to a composition comprising 10-Hydroxy-2-decenoic acid or a derivative thereof, and docosahexaenoic acid for treating fertility-related disorders wherein the 10-Hydroxy-2-decenoic acid or derivative thereof is administered in an amount of about 0.2 mg/day to about 5000 mg/day and the docosahexaenoic acid is administered in an amount of about 100 mg/day to about 4000 mg/day.

Another embodiment is directed to a composition comprising 10-Hydroxy-2-decenoic acid or a derivative thereof, and at least one polyunsaturated fatty acid (PUFA) for treating fertility-related disorders wherein the 10-Hydroxy-2-decenoic acid or derivative thereof is administered in an amount of about 12 mg/day to about 300 mg/day and the PUFA is administered in an amount of about 100 mg/day to about 1500 mg/day.

Another embodiment is directed to a composition comprising 10-Hydroxy-2-decenoic acid or a derivative thereof, and docosahexaenoic acid for treating fertility-related disorders wherein the 10-Hydroxy-2-decenoic acid or derivative thereof is administered in an amount of about 12 mg/day to about 300 mg/day and the docosahexaenoic acid is administered in an amount of about 100 mg/day to about 1500 mg/day.

Preferably, the fertility-related disorder comprises idiosyncratic infertility, polycystic ovarian syndrome, and primary ovarian insufficiency.

In some embodiments, the 10-Hydroxy-2-decenoic acid or derivative thereof is administered in an amount of about 0.2 mg/day to about 5000 mg/day, in an amount of about 0.4 mg/day to about 4500 mg/day, in an amount of about 0.6 mg/day to about 4000 mg/day, in an amount of about 0.8 mg/day to about 3500 mg/day, in an amount of about 1 mg/day to about 3000 mg/day, in an amount of about 2 mg/day to about 2500 mg/day, in an amount of about 3 mg/day to about 2000 mg/day, in an amount of about 4 mg/day to about 1500 mg/day, in an amount of about 5 mg/day to about 1000 mg/day, in an amount of about 6 mg/day to about 900 mg/day, in an amount of about 7 mg/day to about 800 mg/day, in an amount of about 8 mg/day to about 700 mg/day, in an amount of about 9 mg/day to about 600 mg/day, in an amount of about 10 mg/day to about 500 mg/day, in an amount of about 11 mg/day to about 400 mg/day, in an amount of about 12 mg/day to about 300 mg/day, in an amount of about 12 mg/day, in an amount of about 15 mg/day, in an amount of about 20 mg/day, in an amount of about 30 mg/day, in an amount of about 40 mg/day, in an amount of about 50 mg/day, in an amount of about 60 mg/day, in an amount of about 70 mg/day, in an amount of about 80 mg/day, in an amount of about 90 mg/day, in an amount of about 100 mg/day, in an amount of about 125 mg/day, in an amount of about 150 mg/day, in an amount of about 175 mg/day, in an amount of about 200 mg/day, in an amount of about 225 mg/day, in an amount of about 250 mg/day, in an amount of about 275 mg/day, in an amount of about 300 mg/day.

In some embodiments, the PUFA is administered in an amount of about 100 mg/day to about 4000 mg/day, in an amount of about 125 mg/day to about 4500 mg/day, in an amount of about 150 mg/day to about 4000 mg/day, in an amount of about 175 mg/day to about 3500 mg/day, in an amount of about 200 mg/day to about 3000 mg/day, in an amount of about 225 mg/day to about 2500 mg/day, in an amount of about 250 mg/day to about 2000 mg/day, in an amount of about 275 mg/day to about 1500 mg/day, in an amount of about 300 mg/day to about 1000 mg/day, in an amount of about 325 mg/day to about 900 mg/day, in an amount of about 100 mg/day, in an amount of about 125 mg/day, in an amount of about 150 mg/day, in an amount of about 175 mg/day, in an amount of about 200 mg/day, in an amount of about 225 mg/day, in an amount of about 250 mg/day, in an amount of about 275 mg/day, in an amount of about 300 mg/day, in an amount of about 325 mg/day, in an amount of about 350 mg/day, in an amount of about 375 mg/day, in an amount of about 400 mg/day, in an amount of about 425 mg/day, in an amount of about 450 mg/day, in an amount of about 475 mg/day, in an amount of about 500 mg/day, in an amount of about 525 mg/day, in an amount of about 550 mg/day, in an amount of about 575 mg/day, in an amount of about 600 mg/day, in an amount of about 625 mg/day, in an amount of about 650 mg/day, in an amount of about 675 mg/day, in an amount of about 700 mg/day, in an amount of about 725 mg/day, in an amount of about 750 mg/day, in an amount of about 775 mg/day, in an amount of about 800 mg/day, in an amount of about 825 mg/day, in an amount of about 850 mg/day, in an amount of about 875 mg/day, in an amount of about 900 mg/day.

In some embodiments, the composition comprising 10-Hydroxy-2-decenoic acid or a derivative thereof and at least one polyunsaturated fatty acid further comprises a pharmaceutically acceptable carrier. In one embodiment, the pharmaceutically acceptable carrier is selected from a solid carrier and a liquid carrier.

Solid carriers include, but are not limited to, for example, powders, tablets, dispersible granules, capsules, cachets, and suppositories. A solid carrier can be one or more substances, which may also act as diluents, flavoring agents, solubilizers, lubricants, suspending agents, binders, or tablet disintegrating agents. A solid carrier can also be an encapsulating material.

Tablets, powders, cachets, and capsules can be used as solid dosage forms suitable for oral administration.

Liquid dosage forms include, but are not limited to, for example, solutions, suspensions, and emulsions.

Disclosed herein are methods for treating anxiety, inflammatory conditions and fertility-related disorders, and for increasing cognitive performance and managing weight, wherein such methods comprise administration of 10-Hydroxy-2-decenoic acid or a derivate thereof. The methods may further comprise administration of at least one polyunsaturated fatty acid.

One embodiment is directed to a method of treating anxiety in a subject in need thereof, comprising administering a therapeutically effective amount of 10-Hydroxy-2-decenoic acid or a derivative thereof. Another embodiment is directed to use of 10-Hydroxy-2-decenoic acid or a derivative thereof for treating anxiety.

Another embodiment is directed to a method of treating an inflammatory condition in a subject in need thereof, comprising administering a therapeutically effective amount of 10-Hydroxy-2-decenoic acid or a derivative thereof. Another embodiment is directed to use of 10-Hydroxy-2-decenoic acid or a derivative thereof for treating an inflammatory condition. Preferably, the inflammatory condition comprises a gastrointestinal disorder. More preferably, the inflammatory condition is colitis.

Another embodiment is directed to a method of increasing cognitive performance in a subject, comprising administering a therapeutically effective amount of 10-Hydroxy-2-decenoic acid or a derivative thereof. Another embodiment is directed to use of 10-Hydroxy-2-decenoic acid or a derivative thereof for increasing cognitive performance. Preferably, the increasing cognitive performance comprises increased speed of learning, improved memory retention, and combinations thereof.

Another embodiment is directed to a method for managing weight in a subject in need thereof, comprising administering a therapeutically effective amount of 10-Hydroxy-2-decenoic acid or a derivative thereof. In one embodiment, the managing weight is managing weight loss. Another embodiment is directed to use of 10-Hydroxy-2-decenoic acid or a derivative thereof for managing weight. In one embodiment, managing weight is managing weight in a subject having a diseased state. In another embodiment, managing weight is weight loss. In one embodiment, the weight loss is associated with aging. In another embodiment, the weight loss is associated with stress.

Another embodiment is directed to a method for treating fertility-related disorders in a subject in need thereof, comprising administering a therapeutically effective amount of 10-Hydroxy-2-decenoic acid or a derivative thereof. Another embodiment is directed to use of 10-Hydroxy-2-decenoic acid or a derivative thereof for treating fertility-related disorders. Preferably, the fertility-related disorder comprises idiosyncratic infertility, polycystic ovarian syndrome, and primary ovarian insufficiency.

In some embodiments, the 10-Hydroxy-2-decenoic acid or derivative thereof is administered in an amount of about 0.2 mg/day to about 5000 mg/day, in an amount of about 0.4 mg/day to about 4500 mg/day, in an amount of about 0.6 mg/day to about 4000 mg/day, in an amount of about 0.8 mg/day to about 3500 mg/day, in an amount of about 1 mg/day to about 3000 mg/day, in an amount of about 2 mg/day to about 2500 mg/day, in an amount of about 3 mg/day to about 2000 mg/day, in an amount of about 4 mg/day to about 1500 mg/day, in an amount of about 5 mg/day to about 1000 mg/day, in an amount of about 6 mg/day to about 900 mg/day, in an amount of about 7 mg/day to about 800 mg/day, in an amount of about 8 mg/day to about 7000 mg/day, in an amount of about 9 mg/day to about 600 mg/day, in an amount of about 10 mg/day to about 500 mg/day, in an amount of about 11 mg/day to about 400 mg/day, in an amount of about 12 mg/day to about 300 mg/day, in an amount of about 12 mg/day, in an amount of about 15 mg/day, in an amount of about 20 mg/day, in an amount of about 30 mg/day, in an amount of about 40 mg/day, in an amount of about 50 mg/day, in an amount of about 60 mg/day, in an amount of about 70 mg/day, in an amount of about 80 mg/day, in an amount of about 90 mg/day, in an amount of about 100 mg/day, in an amount of about 125 mg/day, in an amount of about 150 mg/day, in an amount of about 175 mg/day, in an amount of about 200 mg/day, in an amount of about 225 mg/day, in an amount of about 250 mg/day, in an amount of about 275 mg/day, in an amount of about 300 mg/day. Preferably, the 10-Hydroxy-2-decenoic acid or derivative thereof is administered in an amount of about 0.2 mg/day to about 5000 mg/day. More preferably, the 10-Hydroxy-2-decenoic acid or derivative thereof is administered in an amount of about 12 mg/day to about 300 mg/day.

The methods disclosed herein may further comprise administering a therapeutically effective amount of at least one polyunsaturated fatty acid (PUFA). Preferably, the PUFA is an omega-3 fatty acid. More preferably, the PUFA is all-cis-docosa-4,7,10,13,16,19-hexaenoic acid, also known as docosahexaenoic acid (DHA).

In some embodiments, the PUFA is administered in an amount of about 100 mg/day to about 4000 mg/day, in an amount of about 125 mg/day to about 4500 mg/day, in an amount of about 150 mg/day to about 4000 mg/day, in an amount of about 175 mg/day to about 3500 mg/day, in an amount of about 200 mg/day to about 3000 mg/day, in an amount of about 225 mg/day to about 2500 mg/day, in an amount of about 250 mg/day to about 2000 mg/day, in an amount of about 275 mg/day to about 1500 mg/day, in an amount of about 100 mg/day, in an amount of about 125 mg/day, in an amount of about 150 mg/day, in an amount of about 175 mg/day, in an amount of about 200 mg/day, in an amount of about 225 mg/day, in an amount of about 250 mg/day, in an amount of about 275 mg/day, in an amount of about 300 mg/day, in an amount of about 325 mg/day, in an amount of about 300 mg/day to about 1000 mg/day, in an amount of about 325 mg/day to about 900 mg/day, in an amount of about 350 mg/day, in an amount of about 375 mg/day, in an amount of about 400 mg/day, in an amount of about 425 mg/day, in an amount of about 450 mg/day, in an amount of about 475 mg/day, in an amount of about 500 mg/day, in an amount of about 525 mg/day, in an amount of about 550 mg/day, in an amount of about 575 mg/day, in an amount of about 600 mg/day, in an amount of about 625 mg/day, in an amount of about 650 mg/day, in an amount of about 675 mg/day, in an amount of about 700 mg/day, in an amount of about 725 mg/day, in an amount of about 750 mg/day, in an amount of about 775 mg/day, in an amount of about 800 mg/day, in an amount of about 825 mg/day, in an amount of about 850 mg/day, in an amount of about 875 mg/day, in an amount of about 900 mg/day. Preferably, the PUFA is administered in an amount of about 100 mg/day to about 4000 mg/day. More preferably, the PUFA is administered in an amount of about 100 mg/day to about 1500 mg/day In some embodiments, the subject preferably is a warm-blooded animal. In some embodiments, the warm-blooded animal is a mammalian species. Exemplary mammalian species include but are not limited to, for example, humans and domestic animals, such as, for example, dogs, cats and horses. Preferred species are humans.

In some embodiments, the subject is a middle-aged animal, wherein "middle-aged" refers to an age at which the animal reaches approximately half its expected life span. For human, this is considered to be about 45 years or older. In some embodiments, the subject is a senior or an aged animal, which means for human to be of 55 years age or older, preferably 60 years or older.

Some of the generally preferred embodiments of the present invention can be described as follows:

The combination of QBA and a C20-C22 PUFA for use in the improvement of cognitive performance of humans, wherein QBA is used in an amount of 0.2-5000 mg per day, preferably 10-500 mg/day, and wherein the C20-C22 PUFA is used in an amount of 100-4000 mg/day, preferably 200-2000 mg/day.

In the above preferred embodiment, the C20-C22 PUFA preferably comprises DHA in at least 50% of the omega-3-PUFA;

In the above preferred embodiments, the DHA is preferably in the form of the ethyl ester or in the form of a tri-glyceride ester;

In the above preferred embodiments, the QBA preferably is in the form of a free fatty acid or salt thereof, or an ethyl ester or glycerol ester, more preferably in the form of a free fatty acid or salt thereof.

The above described preferences apply equally to the other disorders described in this specification, including inflammatory conditions, fertility related disorders, anxiety, cognitive function, and managing weight.

EXAMPLES

Example 1

The concentration-response characteristics of 10-Hydroxy-2-decenoic acid's (Queen Bee Acid; QBA) potential neurodevelopmental and brain health benefits were assessed in vitro.

Neurons from the brain's hippocampus were derived from embryonic day (E17) rat pups and incubated with QBA for 7 days. The cultures were then stained with neuron-specific marker, microtubule associated protein-2a (Map2a) and cell nuclei were stained with 4',6-diamidino-2-phenylindole (DAPI). Fluorescent images of the staining were then captured with a confocal microscope. The staining was quantitated by dividing the percent area of the Map2a staining by the number of neurons. As shown by the results in Table 1, QBA increased the growth of brain cells in culture.

TABLE 1

In vitro Neurite Extension

| QBA Dose (μM) | % Map2a Staining/Neuron |
|---|---|
| 0.00 | 0.24 |
| 0.10 | 0.29 |
| 0.30 | 0.32 |
| 1.00 | 0.30 |
| 3.00 | 0.31 |
| 10.00 | 0.32 |
| 30.00 | 0.32 |
| 100.00 | 0.27 |

Neurons from the brain's hippocampus were derived from E17 pups and incubated for 7 days. The cells were pre-treated with QBA for 48 hours and subsequently challenged with glutamate (25 μM) for 24 hours. The cultures were then stained with propidium iodide, a marker of cell death, and with tetramethylrhodamine ethyl ester (TMRE), a marker for mitochondrial health. The fluorescence of each of these markers was then quantitated with a fluorimeter. As shown by the results in Tables 2 and 3, QBA decreased cell death and increased cell health after the age-related neurodegenerative insult of glutamate toxicity.

TABLE 2

Cell Death

| QBA Dose (μM) | Cell Death (% Control) |
|---|---|
| 0.00 | 100.00 |
| 0.10 | 92.52 |
| 0.30 | 90.43 |
| 1.00 | 88.78 |
| 3.00 | 94.07 |
| 10.00 | 92.78 |
| 30.00 | 90.69 |
| 100.00 | 91.76 |

TABLE 3

Mitochondrial Health

| QBA Dose (μM) | Mitochondrial Health (% Control) |
|---|---|
| 0.00 | 100.00 |
| 0.10 | 101.94 |
| 0.30 | 112.27 |
| 1.00 | 110.50 |
| 3.00 | 106.39 |
| 10.00 | 111.02 |
| 30.00 | 114.72 |
| 100.00 | 123.80 |

Neurons from the brain's hippocampus were derived from E17 pups and incubated for 7 days. The neurons were then pre-treated with QBA for 48 hours and subsequently exposed to a hypoxia (<0.3% $O_2$) for 48 hours. The cultures were stained with calcein AM, a marker of live cells, and with ethidium homodimer, a marker for dead cells. The fluorescence of each of these markers was then quantitated with a fluorimeter.

As shown by the results in Tables 4 and 5, QBA decreased cell death and increased cell health after the age-related insult of low oxygen exposure.

TABLE 4

In vitro Hypoxia Cell Death

| QBA Dose (μM) | Cell Death (% Control) |
|---|---|
| 0.00 | 100.00 |
| 0.10 | 86.26 |
| 0.30 | 83.62 |
| 1.00 | 83.00 |
| 3.00 | 82.20 |
| 10.00 | 85.13 |
| 30.00 | 82.29 |
| 100.00 | 86.39 |

TABLE 5

In vitro Cell Health

| QBA Dose (μM) | Cell Viability (% Control) |
|---|---|
| 0.00 | 100.00 |
| 0.10 | 109.72 |
| 0.30 | 112.76 |
| 1.00 | 118.80 |
| 3.00 | 121.04 |
| 10.00 | 117.65 |

TABLE 5-continued

| In vitro Cell Health | |
|---|---|
| QBA Dose (µM) | Cell Viability (% Control) |
| 30.00 | 115.05 |
| 100.00 | 111.82 |

Example 2

The dose-response characteristics of 10-Hydroxy-2-decenoic acid's (QBA's) potential brain health benefits during aging were assessed for mood in older rats (18-20 months old).

Rats were fed QBA and subjected to an elevated plus-maze. The elevated plus-maze was elevated ~85 cm above the floor and consisted of two open and two closed arms of the same size (50×10 cm). The closed arms were surrounded by walls 40 cm high, and the arms were constructed of black acrylic slabs that radiated from a central platform (10×10 cm) to form a plus sign. Each rat was placed in the central platform facing one of the open arms, and its behavior was recorded during a 5-min testing period with video capture software. More time spent in the open arms is an indication of reduced anxiety-like state. Rats were tested at 18 months old (N=11-13 per group).

In the open field test each rat was placed in a novel environment consisting of an arena measuring 100×100×40 cm. Rats were placed in the middle of the chamber and behavior in the open field was recorded for thirty minutes with a digital camera and measured by software. More time spent in the center of the area is an indication of a reduced anxiety-like state. Rats were tested at 15 months old (N=11-12 per group). QBA (24 mg/kg/d) decreased anxiety in 15-18-month old male rats as measured by the time in the open arms of the elevated plus maze (Table 5) and by the number of center entries in the open field arena (Table 6).

TABLE 5

| Time in Open Arms - Elevated Plus Maze | |
|---|---|
| QBA Dose (mg/kg/day) | Time (s) in Open Arm |
| 0 | 15.2 |
| 0.4 | 48.5 |
| 4 | 52.2 |
| 12 | 37.1 |
| 24 | 69.8 |

TABLE 6

| Center Entries - Open Field | |
|---|---|
| QBA Dose (mg/kg/day) | Center Entries (#) |
| 0 | 1.46 |
| 0.4 | 1.82 |
| 4 | 2.50 |
| 12 | 1.82 |
| 24 | 3.75 |

Example 3

The dose-response characteristics of 10-Hydroxy-2-decenoic acid's (QBA's) in combination with DHA for potential brain health benefits during aging were assessed for mood in 19-20 month-old male rats (N=11-14 per group). Rats were fed QBA alone or QBA+DHA and subjected to an elevated plus-maze.

QBA+DHA decreased anxiety in rats similar to QBA alone as measured by the time in the open arms of the elevated plus maze (Table 7).

TABLE 7

| Time in Open Arms - Elevated Plus Maze | | |
|---|---|---|
| QBA Dose (mg/kg/day) | DHA Dose (% weight of diet) | Time (s) in Open Arm |
| 0 | 0.00 | 4.1 |
| 12 | 0.00 | 31.7 |
| 24 | 0.00 | 31.7 |
| 0 | 0.07% | 32.4 |
| 12 | 0.07% | 36.3 |
| 24 | 0.07% | 34.8 |

Example 4

Cultures of the RAW264.7 mouse macrophage cell line were pre-treated with 10-Hydroxy-2-decenoic acid (QBA) for 1 hour prior to stimulation with lipopolysaccharide (LPS, 100 ng/mL). After 24 hours of incubation, interleukin 13 (IL-1β) and tumor necrosis factor-α (TNFα) levels were determined by Luminex technology and cell numbers were measured using Alamar Blue. Results are given as a ratio of cytokine concentration/cell number.

As shown in Tables 9 and 10, QBA reduced the production of IL-1β and TNFα in immune cells.

TABLE 9

| IL-1β levels | |
|---|---|
| QBA Dose (µM) | IL-1β (pg/mL)/Cell Numbers |
| 0 | 0.00406 |
| 50 | 0.00386 |
| 100 | 0.00402 |
| 500 | 0.00242 |
| 1000 | 0.00242 |
| 2500 | 0.00097 |
| 5000 | 0.00067 |
| Dexamethasone | 0.0013 |

TABLE 10

| TNFα levels | |
|---|---|
| QBA Dose (µM) | TNFα (pg/mL)/Cell Numbers |
| 0 | 0.585 |
| 50 | 0.409 |
| 100 | 0.456 |
| 500 | 0.427 |
| 1000 | 0.261 |
| 2500 | 0.252 |
| 5000 | 0.150 |
| Dexamethasone | 0.153 |

Example 5

Human peripheral blood mononuclear cells (PBMC) were pre-treated with 10-Hydroxy-2-decenoic acid (QBA) for 1 hour prior to stimulation with αCD3/CD28. After 72 hours of incubation, cell number was assessed by Cell Titer Glow.

As shown by the results in Table 11, concentrations of greater than 500 μM reduced the proliferation of human immune cells.

TABLE 11

Proliferation of PBMC

| QBA Dose (μM) | Cell Numbers |
|---|---|
| 0 | 563265 |
| 50 | 517020 |
| 100 | 472678 |
| 500 | 442008 |
| 1000 | 344026 |
| 2500 | 104291 |
| 5000 | 1601 |
| Cyclosporine | 79667 |

Example 6

The dose-response characteristics of 10-Hydroxy-2-decenoic acid's (QBA's) potential brain health benefits during aging were assessed for cognitive performance in older male rats (16-17 months old; N=10-12 per group). Rats were fed QBA for 4-5 months prior to behavioral assessment. Spatial learning and memory performance was tested using the Barnes circular maze which consists of a 4-ft diameter, gray circular platform raised 90 cm above the floor level with 20 holes, 10 cm in diameter, evenly spaced around the circumference. Animals were trained to locate a black escape tunnel beneath one of the holes in response to aversive light stimuli. The latency to enter the escape box in each of two trials across four trial days was recorded. Shorter latencies across and within trial days is an indication of better cognitive performance.

As shown by the results in Table 12, QBA increased the speed of learning acquisition in older (aged 16-17 months old) male rates as measured by the Barnes maze task.

TABLE 12

Learning Acquisition - Barnes maze task
QBA Dose (mg/kg/day)

| Trial Day | 0 | 0.4 | 4 | 12 | 24 |
|---|---|---|---|---|---|
| | Escape Latency (s)* | | | | |
| 1 | 98.4 | 98.8 | 106.7 | 79.3 | 109.8 |
| 2 | 65.9 | 63.4 | 43.4 | 30.7 | 48.4 |
| 3 | 66.8 | 63.4 | 43.4 | 30.7 | 48.4 |
| 4 | 41.7 | 24.7 | 23.6 | 24.3 | 34.3 |

*Values are the average of two trial runs

Example 7

Aged male rats were fed 10-Hydroxy-2-decenoic acid (QBA) for approximately 7 months from 11-months to 18-months of age and the weight of rats was recorded.

QBA helped to maintain healthy body weight in a cohort of aging male rats (N=11-14 per group). The data was analyzed using a repeated measures ANOVA and the data showed a small but significant increase for all doses versus the control (0 mg/kg/day QBA).

TABLE 13

Weight
QBA Dose (mg/kg/day)

| Study Day | 0 Avg Wt (g) | 0.4 Avg Wt (g) | 4 Avg Wt (g) | 12 Avg Wt (g) | 24* Avg Wt (g) |
|---|---|---|---|---|---|
| 0 | 528.5 | 509.6 | 509.8 | 508.7 | 516.8 |
| 7 | 502.1 | 516.1 | 518.9 | 508.8 | 510.9 |
| 21 | 507.8 | 524.4 | 527.4 | 508.0 | 530.8 |
| 29 | 502.6 | 508.6 | 511.6 | 490.2 | 512.3 |
| 36 | 520.6 | 523.1 | 526.8 | 511.7 | 546.4 |
| 50 | 555.6 | 554.6 | 567.3 | 554.3 | 574.6 |
| 57 | 557.0 | 559.5 | 571.0 | 551.4 | 586.8 |
| 64 | 572.5 | 566.7 | 576.4 | 567.6 | 594.2 |
| 71 | 565.6 | 568.6 | 576.2 | 574.1 | 598.5 |
| 78 | 567.5 | 570.3 | 584.8 | 573.1 | 600.7 |
| 85 | 577.2 | 577.3 | 587.5 | 574.6 | 608.8 |
| 92 | 578.6 | 581.3 | 584.3 | 581.2 | 614.9 |
| 99 | 582.4 | 583.8 | 595.4 | 584.5 | 618.1 |
| 106 | 585.6 | 592.7 | 592.5 | 591.2 | 626.7 |
| 113 | 585.9 | 593.2 | 594.7 | 591.2 | 628.4 |
| 120 | 584.4 | 596.8 | 592.2 | 586.1 | 628.6 |
| 127 | 588.1 | 590.7 | 592.4 | 593.3 | 630.3 |
| 141 | 606.2 | 589.8 | 593.1 | 595.8 | 632.0 |
| 148 | 595.2 | 578.0 | 588.0 | 592.9 | 635.4 |
| 155 | 597.2 | 585.4 | 587.8 | 591.1 | 636.3 |
| 162 | 594.0 | 593.6 | 589.5 | 580.5 | 637.3 |
| 169 | 596.2 | 601.7 | 594.0 | 588.2 | 628.4 |
| 176 | 620.5 | 573.6 | 601.7 | 593.0 | 643.9 |
| 182 | 603.4 | 588.7 | 588.0 | 590.6 | 646.0 |
| 190 | 604.4 | 584.1 | 597.8 | 599.5 | 649.5 |
| 197 | 602.3 | 582.6 | 597.7 | 600.8 | 653.3 |
| 204 | 599.8 | 580.1 | 601.8 | 595.5 | 644.4 |
| 211 | 597.3 | 575.8 | 596.6 | 599.6 | 647.8 |
| 217 | 597.2 | 582.6 | 595.9 | 593.7 | 650.6 |

*Significantly different ($p < 0.05$) in Tukey's post hoc test from control

Example 8

Aged male rats were fed 10-Hydroxy-2-decenoic acid (QBA) for approximately 7 months from 12-months to 20-months of age and the weight of rats was recorded.

QBA helped to maintain healthy body weight in a cohort of aging male rats (N=11-14 per group). The data was analyzed using a repeated measures ANOVA and the data showed a small but significant increase for all doses versus the control (0 mg/kg/day QBA or 0 mg/kg/day QBA+0.07% DHA).

TABLE 14

Weight

| DHA (% weight of diet) | QBA Dose (mg/kg/day) | | | | | |
|---|---|---|---|---|---|---|
| | 0 | 12 | 24 | 0 | 12 | 24 |
| | 0.00 | 0.00 | 0.00 | 0.07% | 0.07% | 0.07% |
| Study Day | Avg Wt (g) | Avg Wt (g) | Avg Wt (g) | Avg Wt (g) | Avg Wt (g) | Avg Wt (g) |
| 0 | 553.2 | 547.0 | 551.5 | 552.9 | 545.6 | 561.8 |
| 4 | 567.8 | 560.9 | 566.8 | 568.8 | 560.0 | 571.4 |
| 11 | 578.6 | 571.5 | 573.4 | 579.8 | 569.4 | 579.8 |
| 18 | 590.1 | 580.1 | 585.7 | 592.4 | 579.7 | 591.6 |
| 25 | 595.8 | 584.5 | 593.1 | 594.4 | 585.6 | 595.6 |
| 32 | 596.4 | 590.8 | 596.0 | 600.5 | 588.2 | 599.8 |
| 39 | 596.4 | 591.7 | 599.7 | 605.1 | 588.7 | 600.1 |
| 46 | 597.4 | 594.3 | 601.5 | 607.2 | 590.9 | 597.7 |
| 53 | 600.3 | 595.4 | 601.8 | 610.6 | 595.5 | 607.4 |
| 60 | 596.2 | 598.7 | 606.5 | 614.6 | 598.3 | 611.0 |
| 67 | 602.8 | 597.8 | 607.5 | 616.2 | 600.5 | 617.5 |
| 74 | 604.0 | 603.7 | 611.8 | 617.6 | 604.2 | 614.5 |
| 81 | 607.7 | 607.3 | 614.5 | 619.7 | 609.9 | 619.8 |

TABLE 14-continued

| | | | Weight | | | |
|---|---|---|---|---|---|---|
| DHA (% | | QBA Dose (mg/kg/day) | | | | |
| weight of diet) Study Day | 0 0.00 Avg Wt (g) | 12 0.00 Avg Wt (g) | 24 0.00 Avg Wt (g) | 0 0.07% Avg Wt (g) | 12 0.07% Avg Wt (g) | 24 0.07% Avg Wt (g) |
| 88 | 609.0 | 608.5 | 617.8 | 623.2 | 611.1 | 619.9 |
| 95 | 612.0 | 612.8 | 620.2 | 624.8 | 614.2 | 621.1 |
| 102 | 616.2 | 614.5 | 623.9 | 629.4 | 616.2 | 623.6 |
| 109 | 617.1 | 617.0 | 627.4 | 632.9 | 619.5 | 625.9 |
| 116 | 621.6 | 617.2 | 630.3 | 636.3 | 624.2 | 626.7 |
| 123 | 613.9 | 617.3 | 629.2 | 631.2 | 622.0 | 626.0 |
| 130 | 612.8 | 616.9 | 630.3 | 635.2 | 620.2 | 625.4 |
| 137 | 615.2 | 621.5 | 633.5 | 633.1 | 624.4 | 629.4 |
| 144 | 619.9 | 619.1 | 642.1 | 632.5 | 626.2 | 627.5 |
| 151 | 624.0 | 620.5 | 638.6 | 634.6 | 625.4 | 633.4 |

Example 9

Aged male rats were fed 10-Hydroxy-2-decenoic acid (QBA) for approximately 7 months from 12-months to 20-months of age and the weight of rats was recorded (N=11-14 per group). During the last month of QBA feeding animals were subjected to the psychological stress of the Barnes maze.

QBA and QBA+DHA mitigated weight loss associated with the psychological stress, but DHA alone did not produce the same results. The data was analyzed using a repeated measures ANOVA and the data showed a small but significant increase for all doses versus the control (0 mg/kg/day QBA or 0 mg/kg/day QBA+0.07% DHA).

TABLE 15

| | | | Weight after Barnes maze | | | |
|---|---|---|---|---|---|---|
| DHA (% weight of diet) Behavior Stress Day | 0 0.00 % Change | 12 0.00 % Change | QBA Dose (mg/kg/day) 24 0.00 % Change | 0 0.07% % Change | 12 0.07% % Change | 24 0.07% % Change |
| 7 | −0.55 | −0.15 | −0.15 | −0.76 | −0.33 | −0.12 |
| 14 | −1.07 | −0.20 | 0.02 | −0.57 | −0.47 | −0.21 |
| 21 | −0.88 | 0.56 | 0.54 | −0.88 | 0.23 | 0.47 |
| 28 | −0.26 | 0.63 | 0.74 | −0.56 | 0.58 | 0.17 |
| 35 | 0.51 | 0.87 | 1.32 | −0.23 | 0.48 | 1.07 |

Example 10

Adult female Long-Evans rats (3 months-old) with abnormal ovulatory cycles were fed diets containing 10-Hydroxy-2-decenoic acid (QBA) or no QBA for six (6) weeks. Female rats having normal ovulatory cycle were used as positive controls and were not fed QBA.

As shown in Table 16, supplementation with QBA at 12 mg/kg/day resulted in a similar proportion of normal to abnormal ovulatory cycle animals as the positive control group.

TABLE 16

| | Ovulatory Cycle Status | |
|---|---|---|
| QBA dose (mg/kg/day) | Ovulatory Cycle Status | |
| | Normal | Abnormal |
| 0 (negative) | 7 | 8 |
| 0.4 | 8 | 7 |
| 4 | 6 | 9 |
| 12 | 11 | 4 |
| 24 | 3 | 12 |
| 0 (positive) | 13 | 2 |

Example 11

Young adult female Long-Evans rats (3 months-old) with abnormal ovulatory cycles were fed diets containing 10-Hydroxy-2-decenoic acid (QBA) or no QBA for eight (8) weeks and then mated with a male rat. Female rats having normal ovulatory cycles were used as positive controls and were not fed QBA. The conception index was determined. The conception index is a measure of conception efficiency and is equal to the number of pregnancies divided by the number of discernable mating sessions multiplied by 100.

As shown by the results in Table 17, supplementation with QBA increased the conception index.

TABLE 17

| Conception Index | |
|---|---|
| QBA dose (mg/kg/day) | Conception Index (%) |
| 0 (negative) | 90.9 |
| 0.4 | 112.5 |
| 4 | 107.7 |
| 12 | 225.0 |
| 24 | 200.0 |
| 0 (positive) | 112.5 |

Example 12

Mice (45 days of age) were fed 60 mg/kg body weight/day QBA (equivalent to 24 mg/kg/d in rats; HED of ~240 mg/day, N=10) or a control diet (N=15) for 28 days. Mice fed QBA had a greater percentage increase in body weight than mice fed the control diet with no differences in food consumption. After 28 days, all 10 of the mice fed QBA and 10 of the 15 control mice were subjected to a cell transfer insult wherein the mice were considered to be in a colitis-related disease state. The undiseased controls (N=5) and the diseased controls (N=10) continued on their control diets, and the diseased QBA-fed animals continued on their QBA diets (60 mg/kg body weight/day QBA), for an additional 49 days.

QBA-treated mice in a diseased state maintained their weight similar to the undiseased control mice and were found to be no different than the undiseased controls. In contrast, the diseased controls lost significant weight in comparison to the undiseased controls over the course of the study.

TABLE 18

Weight Management

| Day | Undiseased Control % Original Wt | Diseased + QBA % Original Wt | Diseased Control % Original Wt |
|---|---|---|---|
| 0 | 0.00 | 0.00 | 0.00 |
| 3 | 2.36 | 1.93 | 0.35 |
| 7 | 4.42 | 5.33 | 4.38 |
| 10 | 4.95 | 9.91 | 7.27 |
| 14 | 4.84 | 9.09 | 7.25 |
| 17 | 3.80 | 9.10 | 6.56 |
| 21 | 8.35 | 12.60 | 9.99 |
| 24 | 11.34 | 15.47 | 12.56 |
| 28* | 13.87 | 16.19 | 15.02 |
| 31 | 14.32 | 18.82 | 15.83 |
| 35 | 16.52 | 20.65 | 16.08 |
| 38 | 16.20 | 19.66 | 14.48 |
| 42 | 18.05 | 21.27 | 17.31 |
| 45 | 21.49 | 22.86 | 20.02 |
| 49 | 22.91 | 24.04 | 21.99 |
| 52 | 21.80 | 24.05 | 19.20 |
| 56 | 21.96 | 22.29 | 18.19 |
| 59 | 24.01 | 21.83 | 17.24 |
| 63 | 26.01 | 23.89 | 16.72 |
| 66 | 24.72 | 22.42 | 16.00 |
| 70 | 26.68 | 22.95 | 16.01 |
| 73 | 28.72 | 21.96 | 15.29 |
| 77 | 27.65 | 20.56 | 17.84 |

What is claimed is:

1. A composition comprising 10-Hydroxy-2-decenoic acid or a derivative thereof, and at least one polyunsaturated fatty acid (PUFA), wherein the PUFA is administered in an amount of about 100 mg/day to about 4000 mg/day, for use in treating anxiety, fertility-related disorders, inflammatory conditions, improving cognitive performance, or managing weight.

2. The composition for use of claim 1, wherein the PUFA is an omega-3 fatty acid.

3. The composition for use according to claim 1, wherein the 10-Hydroxy-2-decenoic acid is administered in an amount of about 0.2 mg/day to about 5000 mg/day.

4. A composition according to claim 1 for use in treating anxiety.

5. A composition according to claim 1 for use in treating fertility-related disorders.

6. The composition for use according to claim 5, wherein the fertility-related disorder comprises idiosyncratic infertility, polycystic ovarian syndrome and primary ovarian insufficiency.

7. A composition according to claim 1 for use in treating an inflammatory condition.

8. The composition for use according to claim 7, wherein the inflammatory condition comprises a gastrointestinal tract disorder.

9. The composition for use according to claim 7, wherein the inflammatory condition is colitis.

10. A composition according to claim 1 for use in increasing cognitive performance.

11. A composition according to claim 1 for managing weight.

12. The composition for use according to claim 11, wherein the managing weight is maintaining weight in a subject having a diseased state.

13. The composition for use according to claim 11, wherein the managing weight is weight loss.

14. The composition for use according to claim 13, wherein the weight loss is associated with aging.

15. The composition for use according to claim 13, wherein the weight loss is associated with stress.

16. Composition for use according to claim 1, wherein the composition is used for treatment of a human.

17. Composition for use according to claim 1, wherein the 10-Hydroxy-2-decenoic acid is in the form of a free fatty acid or salt thereof.

18. Composition for use according to claim 17, wherein the PUFA is in the form of an ethyl ester or a glyceride ester.

19. A composition comprising about 0.2 mg to about 5000 mg 10-Hydroxy-2-decenoic acid and about 100 mg to about 4000 mg DHA.

20. A composition according to claim 19, wherein the composition is in the form of one or more capsules.

21. A method of treating anxiety, fertility-related disorders, inflammatory conditions, improving cognitive performance, or managing weight in a subject in need thereof, comprising administering a therapeutically effective amount of 10-Hydroxy-2-decenoic acid or a derivative thereof, and at least one polyunsaturated fatty acid (PUFA).

22. The composition for use of claim 2, wherein the PUFA is docosahexaenoic acid (DHA).

23. A composition comprising about 12 mg to about 300 mg 10-Hydroxy-2-decenoic acid and about 100 mg to about 1500 mg DHA.

24. A composition according to claim 23, wherein the 10-Hydroxy-2-decenoic acid is in the form of a free fatty acid or salt thereof.

25. A composition according to claim 23 or claim 24, wherein the DHA is in the form of an ethyl ester or a glyceride ester.

* * * * *